United States Patent
Arima

(10) Patent No.: US 9,661,729 B2
(45) Date of Patent: May 23, 2017

(54) RADIATION IMAGING SYSTEM, METHOD FOR CONTROLLING THE SYSTEM, AND COMPUTER-READABLE MEDIUM STORING PROGRAM THEREFOR

(75) Inventor: Keisuke Arima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 840 days.

(21) Appl. No.: 13/404,854

(22) Filed: Feb. 24, 2012

(65) Prior Publication Data

US 2012/0219119 A1  Aug. 30, 2012

(30) Foreign Application Priority Data

Feb. 28, 2011  (JP) .................................. 2011-042539

(51) Int. Cl.
*H05G 1/28* (2006.01)
*A61B 6/00* (2006.01)

(52) U.S. Cl.
CPC ................ *H05G 1/28* (2013.01); *A61B 6/461* (2013.01); *A61B 6/467* (2013.01); *A61B 6/468* (2013.01)

(58) Field of Classification Search
CPC .... G06F 19/321; G06F 19/3406; G06F 3/048; G06F 19/32; G06F 19/324; G06F 19/327;
(Continued)

(56) References Cited

U.S. PATENT DOCUMENTS

2001/0011713 A1*  8/2001  Nagatsuka et al. ........... 250/584
2003/0142859 A1*  7/2003  Okuzawa ............ G06F 19/3406 382/132

(Continued)

FOREIGN PATENT DOCUMENTS

JP  2004-154560 A  6/2004
JP  2004-298217 A  10/2004
(Continued)

OTHER PUBLICATIONS

Ulzheimer et al., Assessment of calcium scoring performance in cardiac computed tomography, 2003, European Radiology, vol. 13, pp. 484-497.*

(Continued)

*Primary Examiner* — David J Makiya
*Assistant Examiner* — John Corbett
(74) *Attorney, Agent, or Firm* — Canon USA, Inc. IP Division

(57) ABSTRACT

A radiation imaging system for applying radiation photography to a patient based on contents of an examination request includes: an image capturing method storage unit configured to prestore at least one image capturing method; a patient information input unit configured to input patient information of the patient subjected to an examination based on the examination request; an extraction unit configured to extract an applicable image capturing method from the image capturing method storage unit based on information accompanying the patient information and examination information; a list display unit configured to display an image capturing method extracted by the extraction unit in list form; and a registration unit configured to, by specifying an image capturing method displayed in the list display unit, register the specified image capturing method as imaging information.

24 Claims, 11 Drawing Sheets

(58) Field of Classification Search
CPC ....... G06F 19/322; G06F 3/0482; A61B 6/00;
A61B 6/465; A61B 6/467; A61B 6/563;
A61B 6/566; A61B 6/5294; G06Q 50/24
USPC .............................................. 378/165; 705/3
See application file for complete search history.

(56) References Cited

U.S. PATENT DOCUMENTS

| 2004/0071258 | A1* | 4/2004 | Okumura et al. | 378/19 |
| 2007/0109294 | A1* | 5/2007 | Gotman et al. | 345/418 |
| 2008/0119717 | A1* | 5/2008 | Profio et al. | 600/407 |

FOREIGN PATENT DOCUMENTS

| JP | 2004-337198 A | 12/2004 |
| JP | 2007275117 A | 10/2007 |

OTHER PUBLICATIONS

Berger et al., Hemorrhagic Transformation of Ischemic Brain Tissue Asymptomatic or Symptomatic? 2001, Stroke, vol. 32, pp. 1330-1335.*

Mori et al., Development of Advanced Single Slice CT Scanner Aquilion, Medical Review, vol. 78, pp. 1-9.*

* cited by examiner

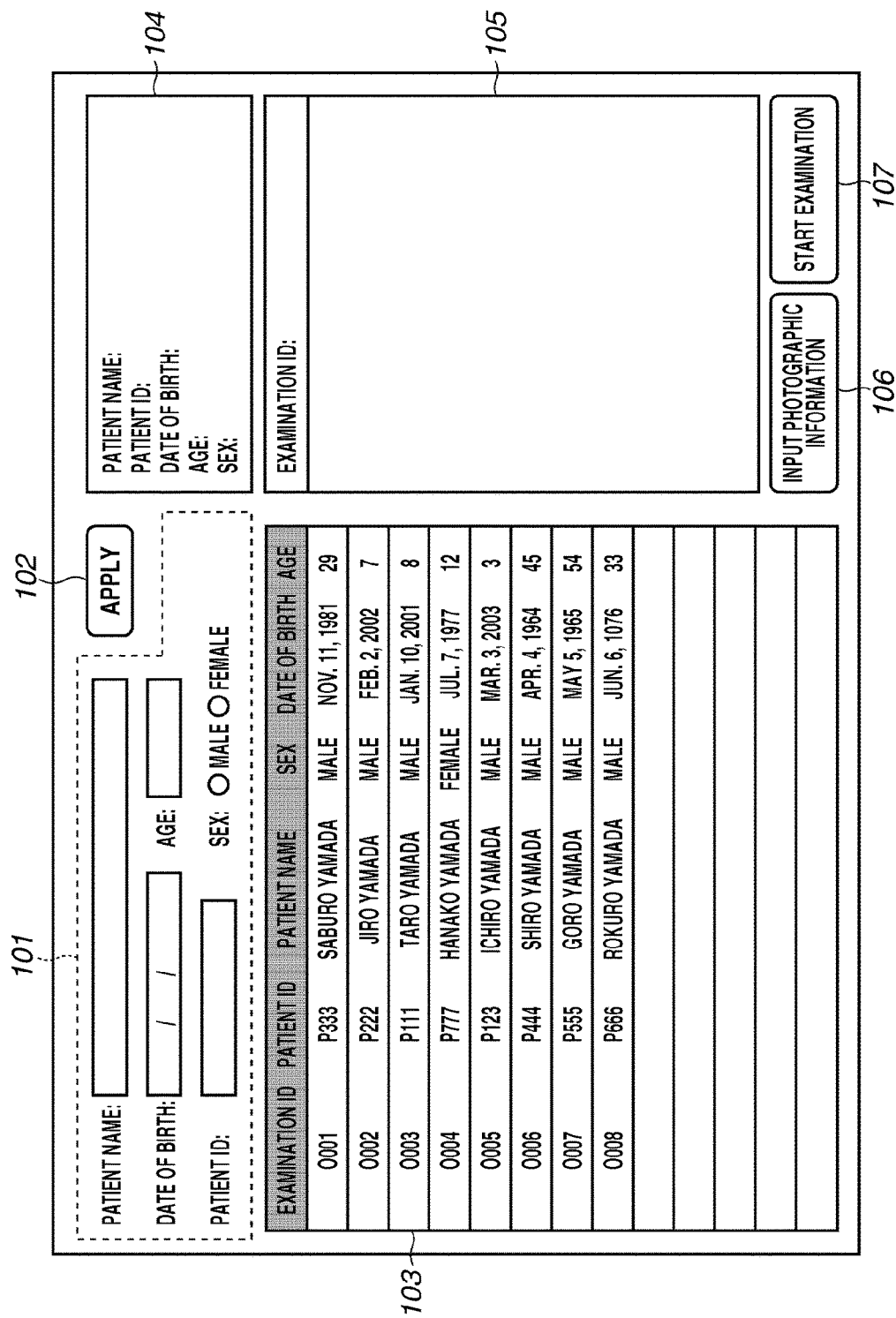

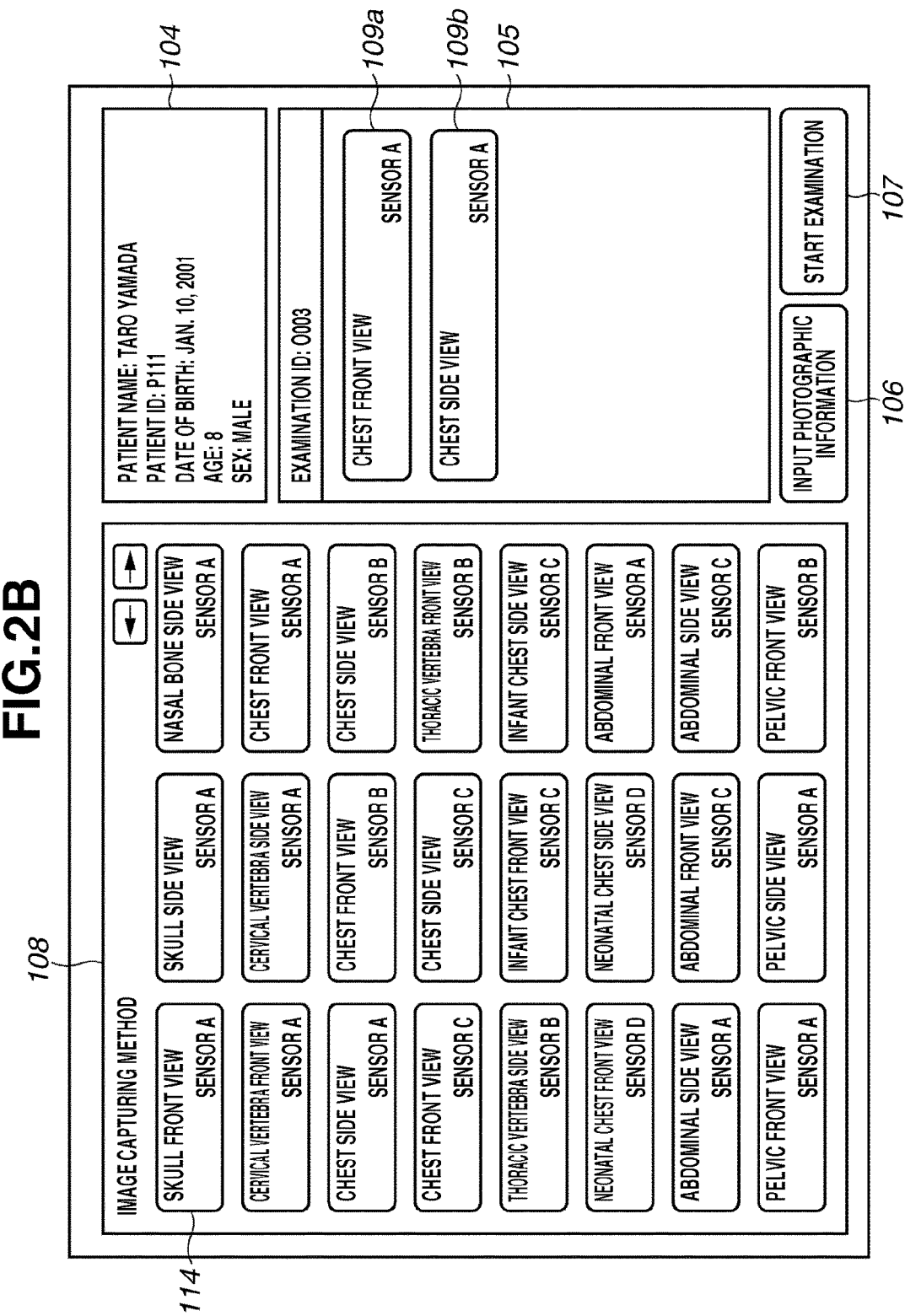

FIG.2C

| | | | | | |
|---|---|---|---|---|---|
| PATIENT NAME: | | | | | |
| DATE OF BIRTH: / / | AGE: | | | | |
| PATIENT ID: | SEX: ○ MALE ○ FEMALE ○ OTHER | | | APPLY | |

| EXAMINATION ID | PATIENT ID | PATIENT NAME | SEX | DATE OF BIRTH | AGE |
|---|---|---|---|---|---|
| 0001 | P333 | SABURO YAMADA | MALE | NOV. 11, 1981 | 29 |
| 0002 | P222 | JIRO YAMADA | MALE | FEB. 2, 2002 | 7 |
| 0003 | P111 | TARO YAMADA | MALE | JAN. 10, 2001 | 8 |
| 0004 | P777 | HANAKO YAMADA | FEMALE | JUL. 7, 1977 | 12 |
| 0005 | P123 | ICHIRO YAMADA | MALE | MAR. 3, 2003 | 3 |
| 0006 | P444 | SHIRO YAMADA | MALE | APR. 4, 1964 | 45 |
| 0007 | P555 | GORO YAMADA | MALE | MAY 5, 1965 | 54 |
| 0008 | P666 | ROKURO YAMADA | MALE | JUN. 6, 1076 | 33 |

PATIENT NAME: TARO YAMADA
PATIENT ID: P111
DATE OF BIRTH: JAN. 10, 2001
AGE: 8
SEX: MALE

EXAMINATION ID: O003

CHEST FRONT VIEW — SENSOR A

CHEST SIDE VIEW — SENSOR A

INPUT PHOTOGRAPHIC INFORMATION

START EXAMINATION

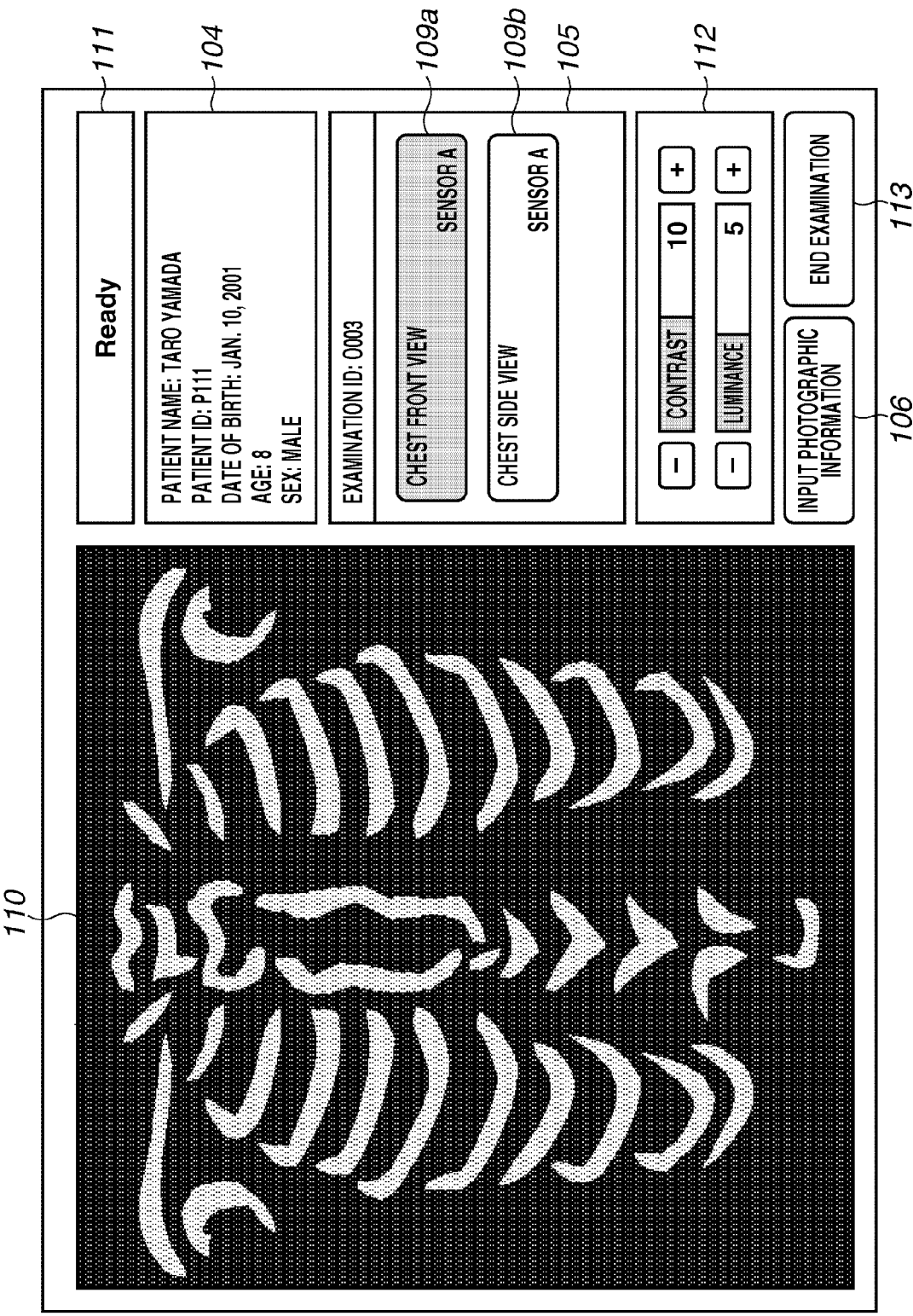

FIG.5A

| EXAMINATION ID | PATIENT ID | PATIENT NAME | DATE OF BIRTH | SEX | EXAMINATION DATE AND TIME | IMAGE ID LIST |
|---|---|---|---|---|---|---|
| O001 | P333 | SABURO YAMADA | NOV. 11, 1981 | MALE | AUG. 8, 2010 | I001, I002, I003 |
| O002 | P222 | JIRO YAMADA | FEB. 2, 2002 | MALE | JUL. 7, 2010 | I201 |
| O003 | P111 | TARO YAMADA | JAN. 10, 2001 | MALE | SRP. 9, 2010 | I101 |

FIG.5B

| IMAGE ID | IMAGE CAPTURING ID | CAPTURED IMAGE STORAGE PATH | IMPLEMENTED PHOTOGRAPHING CONDITIONS | IMPLEMENTED IMAGE PROCESSING CONDITIONS |
|---|---|---|---|---|
| I001 | B001 | C:¥Image¥I001.raw | 120kV, 60mA, ... | CONTRAST 3, LUMINANCE 5, ... |
| I002 | B003 | C:¥Image¥I002.raw | 110kV, 65mA, ... | CONTRAST 5, LUMINANCE 8, ... |
| I003 | B006 | C:¥Image¥I003.raw | 115kV, 55mA, ... | CONTRAST 2, LUMINANCE 3, ... |
| I201 | B002 | C:¥Image¥I201.raw | 120kV, 65mA, ... | CONTRAST 4, LUMINANCE 7, ... |
| I101 | B001 | C:¥Image¥I101.raw | 100kV, 50mA, ... | CONTRAST 7, LUMINANCE 5, ... |

FIG.5C

| IMAGE CAPTURING ID | RADIATION DETECTOR ID | IMAGE CAPTURING METHOD NAME | PHOTOGRAPHING CONDITIONS | IMAGE PROCESSING CONDITIONS | NUMBER OF IMAGE CAPTURES IN THE MORNING | NUMBER OF IMAGE CAPTURES IN THE AFTERNOON | PHYSIQUE INFORMATION |
|---|---|---|---|---|---|---|---|
| B001 | S001 | CHEST FRONT VIEW | 120kV, 60mA, ... | CONTRAST 3, LUMINANCE 5, ... | 70 | 40 | ADULT |
| B002 | S002 | INFANT CHEST FRONT VIEW | 110kV, 65mA, ... | CONTRAST 5, LUMINANCE 8, ... | 15 | 17 | CHILD |
| B003 | S001 | CHEST SIDE VIEW | 115kV, 55mA, ... | CONTRAST 2, LUMINANCE 3, ... | 44 | 60 | ADULT |
| B004 | S001 | ABDOMINAL FRONT VIEW | 120kV, 65mA, ... | CONTRAST 4, LUMINANCE 7, ... | 50 | 10 | ADULT |
| B005 | S002 | INFANT ABDOMINAL FRONT VIEW | 100kV, 50mA, ... | CONTRAST 7, LUMINANCE 5, ... | 20 | 18 | CHILD |
| B006 | S003 | ABDOMINAL FRONT VIEW | 120kV, 65mA, ... | CONTRAST 2, LUMINANCE 3, ... | 30 | 80 | ADULT |

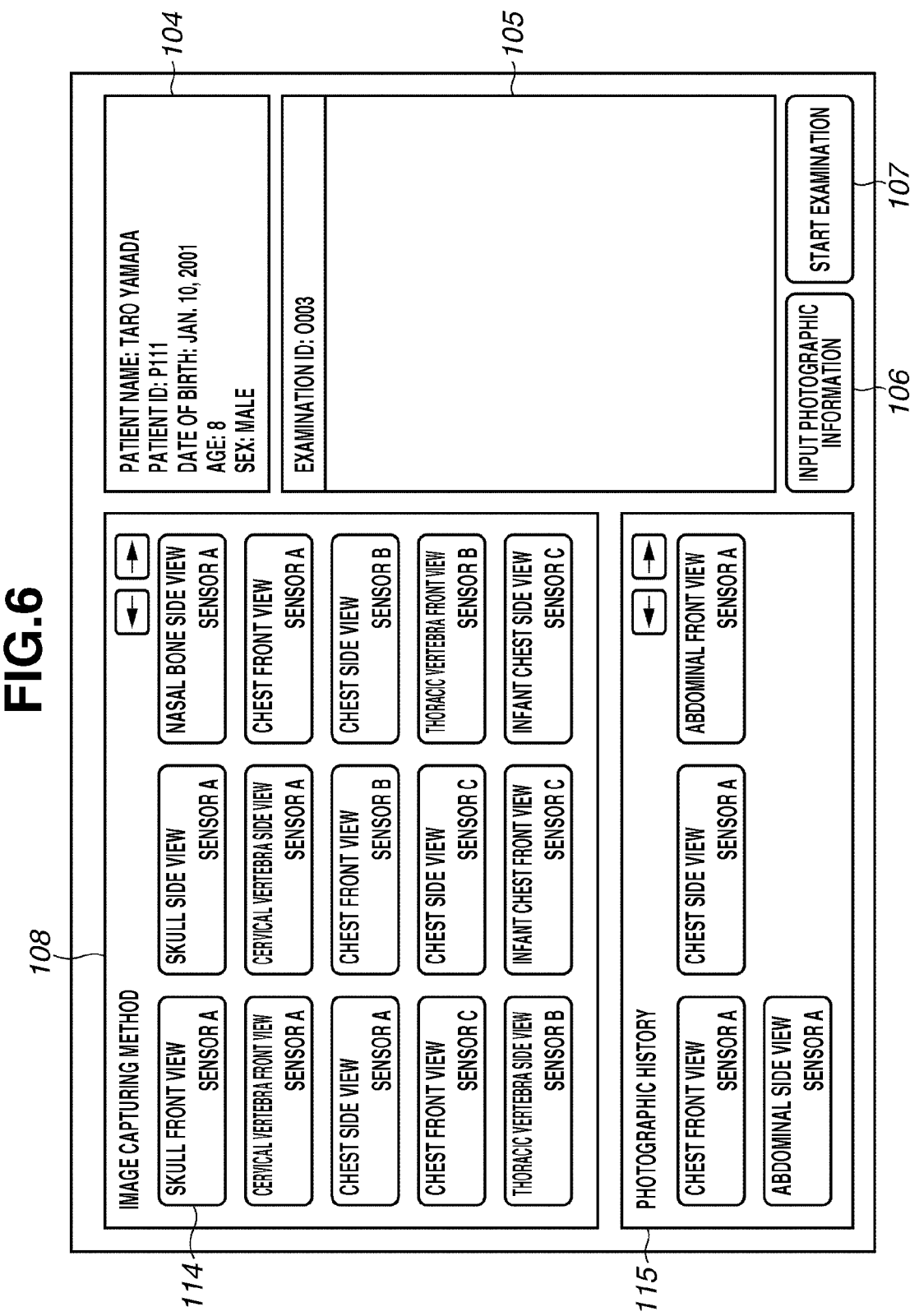

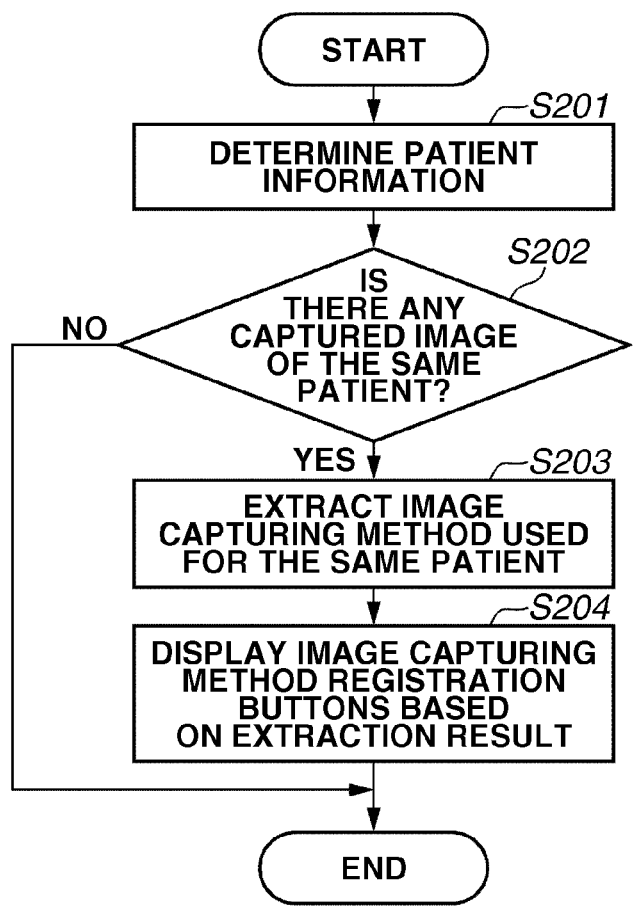

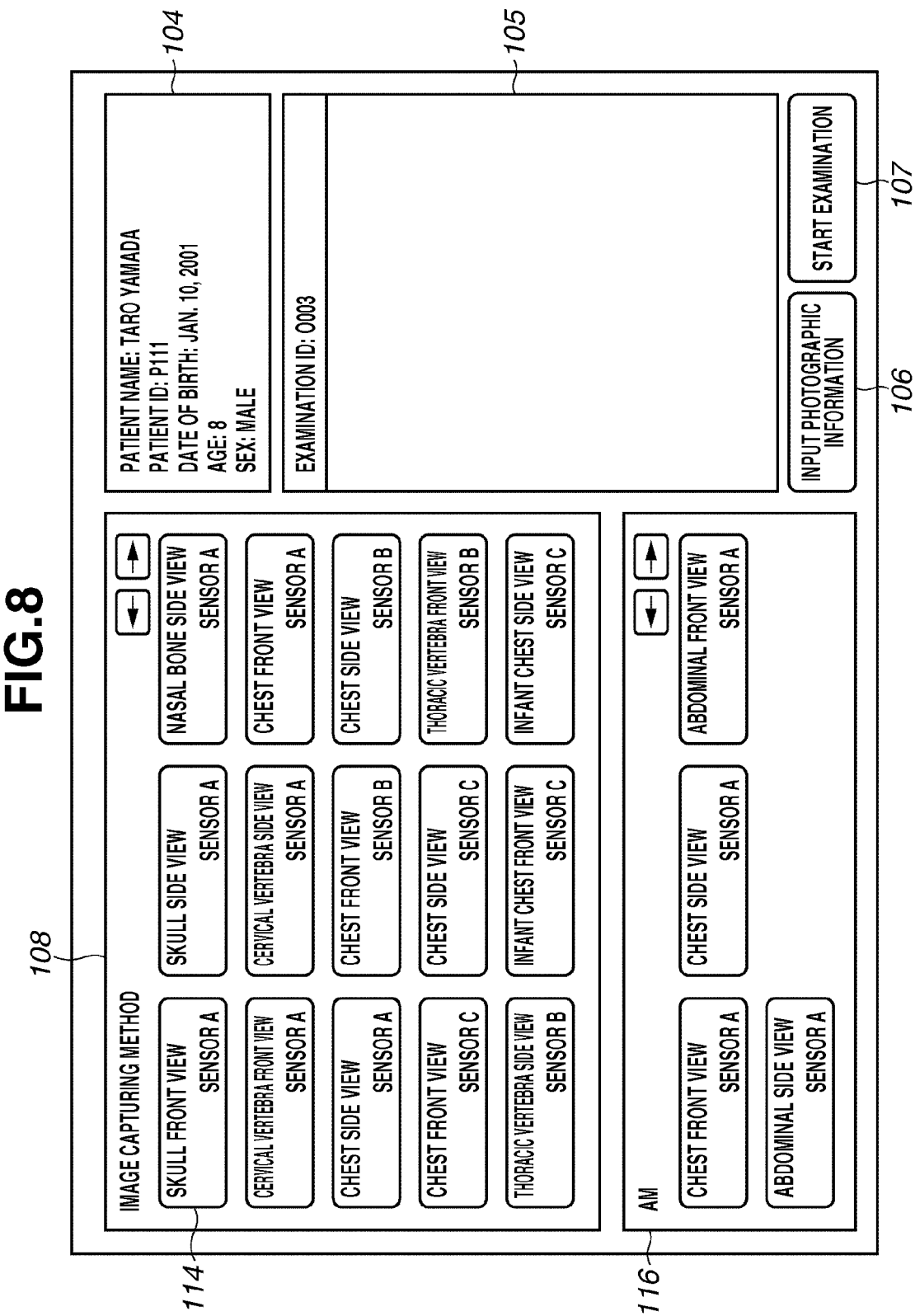

RADIATION IMAGING SYSTEM, METHOD FOR CONTROLLING THE SYSTEM, AND COMPUTER-READABLE MEDIUM STORING PROGRAM THEREFOR

BACKGROUND OF THE INVENTION

Field of the Invention

The present invention relates to a radiation imaging system configured to apply radiation photography to a subject based on contents of an examination request, a method for controlling the radiation imaging system, and a program for causing a computer to execute the method for controlling the radiation imaging system.

Description of the Related Art

A conventionally known radiation imaging apparatus irradiates an object with radiation (for example, X-ray radiation), and detects an intensity distribution of the radiation having penetrated the object to capture a radiation image of the object. Such radiation imaging apparatuses are used mainly in the medical and industrial fields. In recent years, a technique for converting radiation having penetrated a subject into an electrical signal to acquire a radiation image as digital data has been widely employed.

For example, in the medical field, radiological medical examinations are performed on a routine basis. Generally in medical examinations using radiation (radiological medical examinations), medical doctors of each branch of medicine create an examination request sheet describing target imaging portions and image capturing methods, and a radiological technician performs the radiological medical examinations according to examination request sheets. Further, some hospitals have an in-house communications network that interconnects various medical apparatuses to facilitate standardization of patient data management. With such a networked environment, a radiation imaging system performs imaging operations in cooperation with a hospital information system (HIS), a radiological information system (RIS), an image server (picture archiving and communication system (PACS)), etc., where examination request sheets and imaging results thereof are transferred, stored and displayed in accordance with the DICOM (digital imaging and communications in medicine) standard.

In a hospital having the in-house communications network, the HIS issues an examination request instead of issuing an examination request sheet by medical doctors. In this case, in the RIS, the department of radiology receives the examination request from the HIS, and performs a radiological medical examination by using the radiation imaging system based on the received examination request.

Upon completion of the radiological medical examination, the radiation imaging system notifies the HIS and RIS of the completion of the examination, and outputs acquired images and examination information to the PACS for archiving. In some cases, the radiation imaging system also outputs the acquired images and examination information onto a display unit or a printer.

In the medical field, patients undergoing radiological medical examinations often require repeated imaging operations, and regulatory entities require that a record of such operations be kept for reference for a predetermined period of time. Therefore, it is convenient to store the patient information and image capturing methods for future use or reference. In relation to radiological medical examinations, Japanese Patent Application Laid-Open No. 2007-275117 discusses a technique for displaying a list of preregistered image capturing methods on a screen and extracting image capturing methods from the image capturing method list, for example, by specifying target imaging portions on a human body model, thus registering the image capturing methods described on the examination request sheet to an examination.

Since photographing conditions and image processing conditions differ according to target imaging portions, imaging orientations, imaging procedures, and radiation detectors used for image capture, a large number of image capturing methods are preregistered in the radiation imaging system. Therefore, an operation for searching for the image capturing methods described in the examination request in the entire list is very time-consuming. In this case, the method for extracting image capturing methods by specifying target imaging portions on a human body model discussed in Japanese Patent Application Laid-Open No. 2007-275117 has been considered to be very effective.

For example, in an examination aiming for observation of patient's medical care process, the method compares a newly captured image with an existing image (a previously captured image) for purposes of evaluating the progress in medical condition of the patient. In this case, to acquire an image suitable for medical care process observation, it is necessary to capture a new image under the same imaging parameters and image processing conditions by using the same radiation detector as the existing image subjected to comparison.

In some hospitals, a radiation imaging system is used, for example, for health examinations in the morning and for clinical examinations in the afternoon. In this case, since examination contents depend on the medical purpose, each time zone has a specific distribution tendency of frequency in use of image capturing methods. Therefore, it is highly desirable that image capturing methods usable for capturing a new image are improved and optimized.

SUMMARY OF THE INVENTION

The present invention is directed to providing a scheme for facilitating procedures for registering image capturing methods.

According to an aspect of the present invention, a radiation imaging system for applying radiation photography to a patient based on contents of an examination request includes: an image capturing method storage unit configured to prestore at least one image capturing method; a patient information input unit configured to input patient information of the patient subjected to an examination based on the examination request; an extraction unit configured to extract an applicable image capturing method from the image capturing method storage unit based on information accompanying the patient information and examination information; a display unit configured to display the image capturing method extracted by the extraction unit in list form; and a registration unit configured to, by specifying the image capturing method displayed in the list display unit, register the specified image capturing method as imaging information.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 2A, 2B, and 2C schematically illustrate example examination input screens according to the first exemplary embodiment of the present invention.

FIG. 3 schematically illustrates an example photographing screen according to the first exemplary embodiment of the present invention.

FIGS. 5A, 5B, and 5C schematically illustrate example table configurations in a storage unit illustrated in FIG. 4.

FIG. 6 schematically illustrates an example display screen according to the first exemplary embodiment of the present invention.

FIG. 7 is a flowchart illustrating example control processing performed by the radiation imaging system (X-ray imaging system) according to the first exemplary embodiment of the present invention.

FIG. 8 schematically illustrates an example display screen according to a second exemplary embodiment of the present invention.

DESCRIPTION OF THE EMBODIMENTS

Various exemplary embodiments, features, and aspects of the invention will be described in detail below with reference to the drawings.

Although, in the exemplary embodiments described below, a case where X-ray is applied as radiation will be described, radiation is not limited thereto, and may be an electromagnetic wave, alpha ray, beta ray, or gamma ray.

Figure 1:
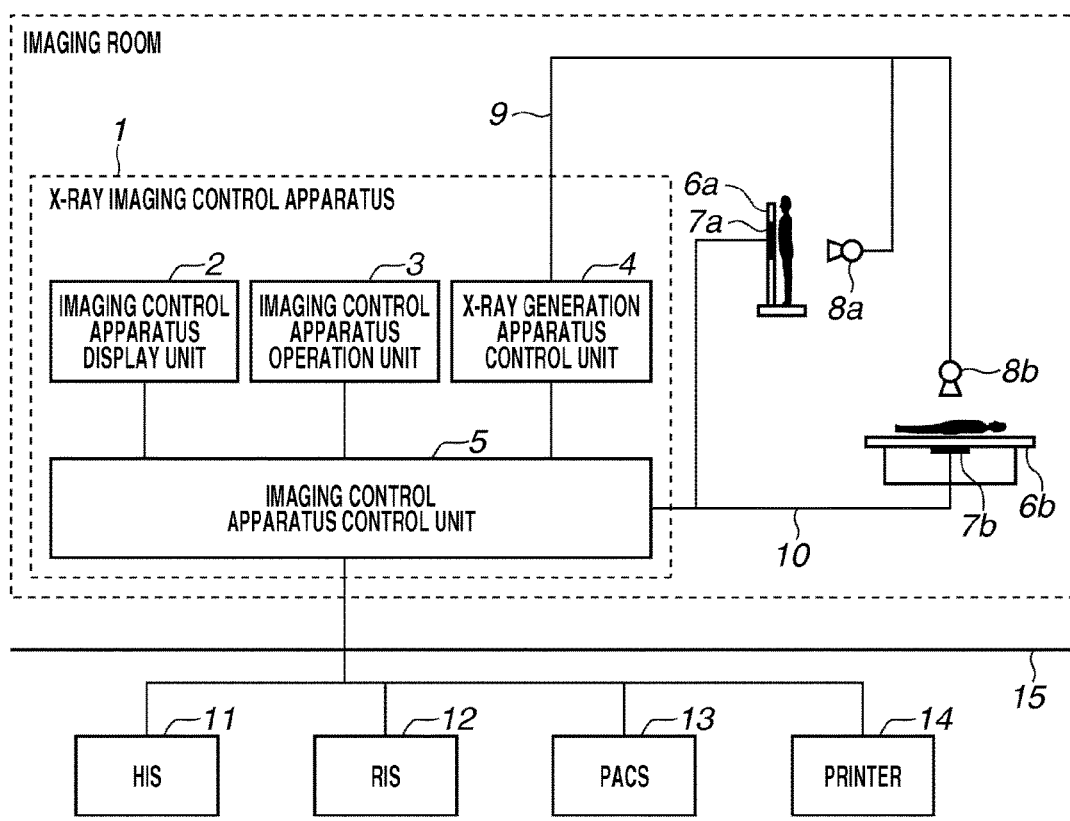
FIG. 1 schematically illustrates an example overall configuration of a radiation imaging system (X-ray imaging system) according to a first exemplary embodiment of the present invention.

A first exemplary embodiment will be described below. FIG. 1 schematically illustrates an example configuration of a radiation imaging system (herein after referred to as X-ray imaging system) according to the first exemplary embodiment of the present invention.

The X-ray imaging system illustrated in FIG. 1 applies X-ray photography (radiography) to a patient's body (subject) based on contents of an examination request. The X-ray imaging system is connected with an X-ray imaging control apparatus 1, an HIS 11, an RIS 12, a PACS (image server) 13, and a printer 14. These apparatuses are connected via a communication unit 15 composed of, for example, a local area network (LAN) and a wide area network (WAN).

Each of these apparatuses includes one or a plurality of computers. Each computer is provided with a main control unit such as a central processing unit (CPU), and a storage unit such as a read-only memory (ROM) and a random access memory (RAM). Each computer may be provided with a communication unit such as a network card, and input and output units such as a keyboard, a display, and a touch panel. These units are connected via a bus, and controlled when the main control unit executes a program stored in the storage unit.

The X-ray imaging control apparatus (radiation imaging control apparatus) 1 includes an imaging control apparatus display unit 2, an imaging control apparatus operation unit 3, an X-ray generation apparatus control unit 4, and an imaging control apparatus control unit 5.

The X-ray generation apparatus control unit (radiation generation apparatus control unit) 4 is connected with X-ray generation apparatuses (radiation generation apparatuses) 8a and 8b via cables 9 to control the irradiation of X-ray (radiation) from the X-ray generation apparatuses 8a and 8b. Each of the X-ray generation apparatuses 8a and 8b functions as a radiation generation unit, and is implemented by using, for example, an X-ray tube. The X-ray generation apparatuses 8a and 8b irradiate a subject (for example, a specific portion of the patient's body) with X-ray.

The imaging control apparatus control unit 5 totally controls the processing of the X-ray imaging control apparatus 1. The imaging control apparatus display unit 2 is implemented by using, for example, a liquid crystal display to display various pieces of information to an operator (radiological technician or medical doctor).

The imaging control apparatus operation unit 3 is implemented by using, for example, a mouse, operation buttons, etc. to input various instructions from the operator to the X-ray imaging control apparatus 1. The imaging control apparatus display unit 2 and the imaging control apparatus operation unit 3 may be integrated into a touch panel.

The X-ray imaging control apparatus 1 is connected with X-ray detection units (radiation detectors) 7a and 7b via cables 10. The X-ray detection units 7a and 7b transmit and receive the power, image signals, and control signals to/from the X-ray imaging control apparatus 1 via the cables 10. Each of the X-ray detection units 7a and 7b detects X-ray having penetrated the subject, and functions as a detection unit for acquiring an X-ray image (radiation image) based on the subject. Specifically, when the X-ray generation apparatuses 8a and 8b and the X-ray detection units 7a and 7b operate in collaboration to achieve an X-ray imaging unit. The X-ray detection units 7a and 7b are installed on a photography platform 6a at an upright position and a photography platform 6b at a recumbent position, respectively.

Although an example configuration of the X-ray imaging system has specifically been described above, the configuration illustrated in FIG. 1 is to be considered as an example and may be suitably changed. For example, referring to FIG. 1, although various apparatuses are connected to the X-ray imaging control apparatus 1 via the communication unit 15, the connection of such apparatuses to the X-ray imaging control apparatus 1 is not indispensable.

Processing for X-ray photography performed by the X-ray imaging system illustrated in FIG. 1 according to an examination flow will be described below.

First of all, based on an examination request sheet or an examination request from the RIS 12, the operator inputs patient information and examination information to the X-ray imaging control apparatus 1 (imaging control apparatus operation unit 3). In this case, the patient information includes a patient name, a patient identifier (ID), etc., and the examination information includes imaging information specifying contents of photography to be applied to the patient.

FIGS. 2A to 2C schematically illustrate an example of examination input screens according to the first exemplary embodiment of the present invention.

The X-ray imaging control apparatus 1 displays the examination input screens illustrated in FIGS. 2A to 2C on the imaging control apparatus display unit 2. The examination input screen in FIG. 2A includes a patient information input area 101, a patient information determination button 102, a requested examination list 103, a patient information display area 104, an imaging information display area 105, an imaging information input button 106, and an examination start button 107. The patient information input area 101 forms a patient information inputting method for inputting the patient information of a patient subjected to an examination.

When performing examination based on an examination request sheet, the operator (radiological technician) inputs the patient information described on the examination request sheet in the patient information input area 101 and presses the patient information determination button 102 to input the patient information. Then, the patient information (patient name, patient ID, date of birth, etc.) corresponding to the input patient is displayed in the patient information display area 104.

As illustrated in FIG. 2B, the imaging information input area 108 is displayed, and the examination ID is displayed in the imaging information display area 105. The operator searches for the image capturing method described on the examination request sheet in an image capturing method list displayed in the imaging information input area 108, and presses an image capturing method registration button 114 to register it to the imaging information display area 105.

When performing an examination based on an examination request from the RIS 12, the operator selects any one of examinations from the requested examination list 103. Then, as illustrated in FIG. 2C, the patient information display area 104 displays the patient information (patient name, patient ID, date of birth, etc.) corresponding to the selected patient. The imaging information display area 105 displays the examination ID, and an area immediately thereunder displays the imaging information corresponding to the examination ID. The imaging information is received from the RIS 12 as described above. Referring to FIGS. 2A to 2C, the image capturing method buttons (a chest front view button (sensor A) 109a and a chest side view button (sensor A) 109b) corresponding to the imaging information are arranged. When the operator presses the imaging information input button 106, the imaging information input area 108 appears, allowing the operator to input additional image capturing methods.

The operator checks the patient information and imaging information and then presses the examination start button 107 to determine examinations to be performed.

FIG. 3 schematically illustrates an example photographing screen according to the first exemplary embodiment of the present invention.

When the operator presses the examination start button 107, the X-ray imaging control apparatus 1 displays the photographing screen illustrated in FIG. 3 on the imaging control apparatus display unit 2. The photographing screen illustrated in FIG. 3 is used at the time of image capture.

Basically, the photographing screen illustrated in FIG. 3 includes similar display areas to those in the examination input screens illustrated in FIGS. 2A to 2C. Newly added display areas are an image display area 110, a message area 111, an image processing setting area 112, and an examination completion button 113, as illustrated in FIG. 3. The image display area 110 forms an image display unit for displaying an X-ray image (radiation image) acquired through image capture.

When the photographing screen illustrated in FIG. 3 is displayed, an image capturing method button 109a arranged at the top of the imaging information display area 105 is selected as a default state. Accordingly, the X-ray imaging control apparatus 1 causes the imaging control apparatus control unit 5 to transmit to the X-ray generation apparatus control unit 4 the photographing conditions (X-ray tube voltage, tube current, irradiation interval, etc.) set in response to the image capturing method button 109a (image capturing method). Based on the photographing conditions, the imaging control apparatus control unit 5 controls the X-ray detection units 7a and 7b to prepare for image capture. When the X-ray imaging control apparatus 1 is prepared for image capture, the X-ray imaging control apparatus 1 enters a state ready for image capture. In this case, a message "Ready" indicating that the X-ray imaging control apparatus 1 is ready for image capture is displayed in the message area 111.

Then, the operator checks the image capturing method, sets up for image capture, and adjusts the patient's position. Upon completion of a series of preparations for image capture, the operator makes sure that the X-ray imaging control apparatus 1 is ready for image capture with reference to the message area 111, and presses an X-ray irradiation switch (not illustrated). Then, the X-ray imaging control apparatus 1 causes the X-ray generation apparatuses 8a and 8b to irradiate the subject (a specific portion of the patient's body) with X-ray, and causes the X-ray detection units 7a and 7b to detect X-ray having penetrated the subject, thus performing X-ray photography.

Upon completion of X-ray photography, the X-ray imaging control apparatus 1 causes the imaging control apparatus control unit 5 to acquire a captured image from the X-ray detection units 7a and 7b, and applies image processing to the acquired image based on predetermined image processing conditions. The predetermined image processing conditions are previously defined for the image capturing method.

Upon completion of image processing, the X-ray imaging control apparatus 1 displays on the image display area 110 the captured image having undergone the image processing. When the operator wants to change the contrast of the captured image, for example, the operator operates contrast and luminance buttons provided in the image processing setting area 112. Thus, the operator can apply additional image processing to the captured image displayed on the image display area 110. When the operator presses an image capturing method button 109 for an uncaptured image, the photographing conditions and image processing conditions for the currently captured image are stored and then next image capture is started.

The operator repeats the above-described procedures to perform all of the image capturing methods in the imaging information display area 105. Upon completion of image capture for all of the image capturing methods, the operator presses the examination completion button 113. Thus, a series of examinations is completed and the X-ray imaging control apparatus 1 redisplays the examination input screens illustrated in FIGS. 2A to 2C. In this case, the X-ray imaging control apparatus 1 causes the imaging control apparatus control unit 5 to output captured images, examination information, etc., for example, to the PACS 13, the printer 14, the RIS 12, and a ROM (not illustrated) in own apparatus. The captured images and patient information are stored, in association with each other, in the RIS 12 and the ROM.

An example functional configuration of the imaging control apparatus control unit 5 illustrated in FIG. 1 will be described below.

Figure 4:
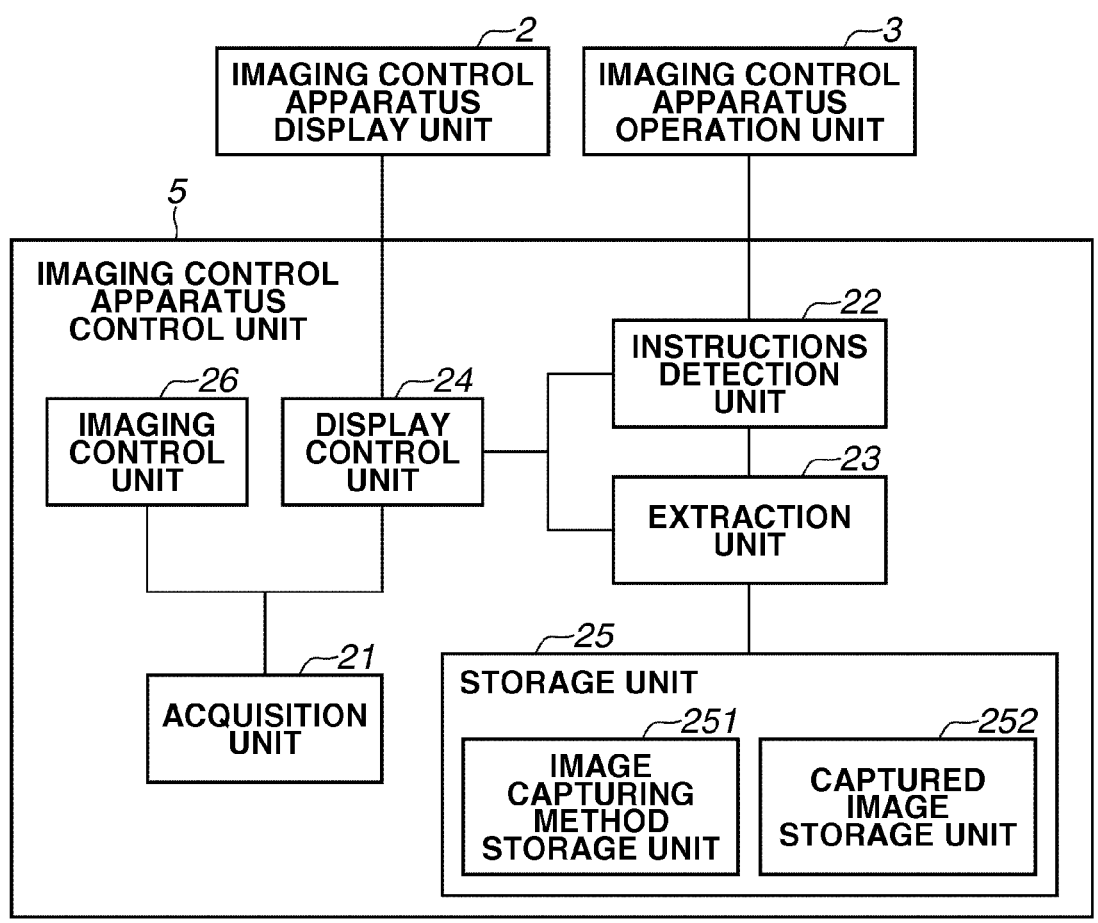
FIG. 4 is a block diagram illustrating an example functional configuration of an imaging control apparatus control unit according to the first exemplary embodiment of the present invention illustrated in FIG. 1.

FIG. 4 is a block diagram illustrating an example functional configuration of the imaging control apparatus control unit 5 illustrated in FIG. 1 according to the first exemplary embodiment of the present invention.

As units for screen display control, the imaging control apparatus control unit 5 includes an acquisition unit 21, an instruction detection unit 22, an extraction unit 23, a display control unit 24, a storage unit 25, and an imaging control unit 26. Furthermore, the imaging control apparatus control unit 5 forms, for example, an examination generation unit for generating an examination based on the patient information and imaging information. Specifically, the imaging control apparatus control unit 5 acquires examination information including the patient information and imaging information which defines contents of photography to be applied to a patient based on the patient information, and generates an examination based on the acquired examination information.

The acquisition unit 21 acquires examination information and other pieces of information required for screen display. For example, the acquisition unit 21 acquires a captured image and patient information associated with the captured image from the ROM of own apparatus, the PACS 13, or the storage unit 25 (a captured image storage unit 252). The captured image is stored in the ROM, the PACS 13, or the storage unit 25 (the captured image storage unit 252) in association with the patient information of the captured image. The acquisition unit 21 acquires, for example, from the ROM the examination information based on an examination request from the RIS 12.

The instruction detection unit 22 detects an instruction for display changeover for the currently displayed screen based on an input operation by the operator. Specifically, when any one of the examination input screens illustrated in FIGS. 2A to 2C is displayed and the operator operates the patient information determination button 102 by using a mouse, the instruction detection unit 22 detects the relevant operation, and notifies the display control unit 24 and the extraction unit 23 that the patient information is determined and specified.

The storage unit 25 includes the image capturing method storage unit 251 and the captured image storage unit 252. The image capturing method storage unit 251 stores one or a plurality of preregistered image capturing methods (image capturing method storage step). The captured image storage unit 252 stores information about completed examinations and captured images (captured image storage step).

FIGS. 5A to 5C schematically illustrate example table configurations in the storage unit 25 illustrated in FIG. 4.

The examination information, image information, and image capturing method information are stored in a database as tables as illustrated in FIGS. 5A, 5B, and 5C, respectively. Specifically, an examination information table illustrated in FIG. 5A defines the examination ID, patient ID, patient name, date of birth, sex, examination date, and image ID list. An image information table illustrated in FIG. 5B defines the image ID, image capturing method ID, captured image storage path, implemented photographing conditions, and implemented image processing conditions. An image capturing method information table illustrated in FIG. 5C defines the image capturing method ID, radiation detector ID, image capturing method name, photographing conditions, image processing conditions, number of image captures in the morning, number of image captures in the afternoon, and physique information.

The imaging control unit 26 controls patient's radiation photography by using, for example, a radiation detector related to the radiation detector ID in the image capturing method information table. The imaging control unit 26 further controls patient's radiation photography based on the photographing conditions in the image capturing method information table. The image display area 110 (FIG. 3) displays, for example, a radiation image having undergone image processing based on the image processing conditions in the image capturing method information table.

When the patient information of the patient subjected to examination is determined, the extraction unit 23 extracts from the storage unit 25 (the image capturing method storage unit 251) one or more image capturing methods satisfying extraction conditions, i.e., information accompanying the patient information and examination information (collateral information). In the present exemplary embodiment, the information accompanying the patient information and examination information is patient identification information (patient name, patient ID, date of birth, etc.). In the present invention, the information accompanying the patient information and examination information is not limited to the patient identification information, and is applicable in the following ways.

Specifically, the extraction unit 23 can apply the information to the extraction from the image capturing method storage unit 251 one or more image capturing method applicable to the physique, for example, based on information about patient's physique accompanying the patient information (the physique information in the image capturing method information table illustrated in FIG. 5C). The extraction unit 23 can apply the information to the extraction from the image capturing method storage unit 251 one or more image capturing methods used frequently in a date zone related to examination date information, for example, based on the examination date information accompanying the examination information (the date and time of examination in the examination information table illustrated in FIG. 5A). The extraction unit 23 can apply the information to the extraction from the image capturing method storage unit 251 one or more image capturing methods registered to a requesting branch of medicine related to branch-of-medicine information, for example, based on requesting branch-of-medicine information accompanying the examination information.

The display control unit 24 generates a display screen (display image) based on the examination information and captured images acquired by the acquisition unit 21. The display control unit 24 includes an extraction result display control unit (not illustrated) for displaying in list form the image capturing methods extracted by the extraction unit 23. For example, suppose that the patient information of a patient A is input to the patient information input area 101. In this case, the extraction unit 23 searches for captured images of the patient A from the captured image storage unit 252, and outputs image capturing methods of the captured images as an extraction result.

FIG. 6 schematically illustrates an example display screen according to the first exemplary embodiment of the present invention. As illustrated in FIG. 6, the display control unit 24 displays the imaging information input area 108 and a imaging history 115 (a list display method) for displaying image capturing methods extracted by the extraction unit 23 in list form. The display control unit 24 further generates and displays image capturing method registration buttons 114 based on an extraction result. When the operator specifies one or more image capturing methods from the list displayed in the imaging history 115, the imaging control apparatus control unit 5 (for example, display control unit 24) registers to the imaging information display area 105 the specified image capturing method as the imaging information (registration method).

The imaging control unit 26 controls the X-ray imaging unit (an X-ray generation apparatus 8 and an X-ray detection unit 7) based on the examination information acquired by the acquisition unit 21. Thus, based on the examination information, the X-ray photography applied to a patient is controlled.

Processing for performing an examination aiming for medical care process observation by the X-ray imaging system illustrated in FIG. 1 will be described below with reference to FIG. 7.

FIG. 7 is a flowchart illustrating example processing procedure of control method performed by the radiation imaging system (X-ray imaging system) according to the first exemplary embodiment of the present invention. Processing performed after the operator completes input of the patient information of the patient subjected to implementation (examination) in the examination input screen will be described below.

In step S201, the imaging control apparatus control unit 5 determines the patient information, and instructs the extraction unit 23 to extract one or more image capturing methods previously used for image captures of the relevant patient. Specifically, based on the examination information table (FIG. 5A), the extraction unit 23 extracts the examination information of the relevant patient for whom the patient information was determined. Then, the extraction unit 23 extracts from the image information table (FIG. 5B) image information of the same image ID as the one included in the extracted examination information.

In step S202, the imaging control apparatus control unit 5 determines whether there exists any captured image of the relevant patient. When there is no image of the relevant patient (NO in step S202), the processing of the flowchart in FIG. 7 proceeds to end.

Otherwise, when there exists an image of the relevant patient (YES in step S202), i.e., a captured image of the patient is extracted, the processing proceeds to step S203.

In step S203, the imaging control apparatus control unit 5 (for example, the extraction unit 23) extracts one or more image capturing methods used for images of the relevant patient. Specifically, for example, the extraction unit 23 extracts from the image capturing method information table (FIG. 5C) the image capturing method ID of the image information of the extracted captured image. In this case, the extraction unit 23 replaces the photographing conditions and image processing conditions in the extracted image capturing method information with the implemented photographing conditions and implemented image processing conditions in the relevant image information, and outputs them to the extraction result display control unit (not illustrated) of the display control unit 24. When there is a plurality of images captured with the same image capturing method, the photographing conditions and image processing conditions can be replaced by the implemented photographing conditions and implemented image processing conditions in the latest image information.

In step S204, the imaging control apparatus control unit 5 (for example, the extraction result display control unit (not illustrated) of the display control unit 24) generates the image capturing method registration buttons 114 based on an extraction result, and updates the screen display. Then, the processing of the flowchart in FIG. 7 proceeds to end.

When the operator presses any one of the image capturing method registration buttons 114 generated and displayed in the imaging information input area 108, the corresponding image capturing method is registered to the imaging information display area 105. Excluding from the imaging information input area 108 and the imaging history 115 the image capturing method registration buttons 114 already added (registered) to the imaging information display area 105, and displaying other image capturing method registration buttons enable preventing duplicated registration of identical image capturing methods and effective use of display areas. The imaging history 115 excludes an image capturing method included in the generated examination from candidates of list display.

When an examination is started, the X-ray imaging control apparatus 1 causes the imaging control apparatus control unit 5 to transmit the implemented photographing conditions of the image capturing method to the X-ray generation apparatus control unit 4. Upon completion of image capture, the imaging control apparatus control unit 5 acquires captured images, and applies image processing to the acquired captured images based on the implemented image processing conditions of the image capturing methods.

According to the first exemplary embodiment, image capturing methods that have been implemented for image capture of the relevant patient are extracted and the image capturing method registration buttons 114 are displayed in the examination input screen as described above, thus facilitating registration of image capturing methods. Further, since implemented information is used for the photographing conditions and image processing conditions of the captured image, a new image can be captured under the same conditions as an existing image subjected to comparison, thus acquiring an image suitable for medical care process observation.

A second exemplary embodiment of the present invention will be described below. The first exemplary embodiment has specifically been described above based on a case where image capturing methods are extracted based on the patient identification information in an examination aiming for medical care process observation. The second exemplary embodiment will be described below based on a case where image capturing methods are extracted based on examination time information in a hospital where the radiation imaging system is operated differently in each time zone.

Suppose that the photographing screen illustrated in FIG. 3 is displayed, and images are captured with the image capturing method for the first image capturing method button 109a. Then, the imaging control apparatus control unit 5 updates the number of image captures by time zone (the number of image captures in the morning and the number of image captures in the afternoon in the example in FIG. 5C) in a relevant image capturing method record in the image capturing method information table (FIG. 5C) according to the image capture time.

When the patient information is determined in the examination input screens illustrated in FIGS. 2A to 2C, the imaging control apparatus control unit 5 causes the extraction unit 23 to extract from the image capturing method information table (FIG. 5C) one or more image capturing methods having a large number of image captures (a high frequency in image capture) in the relevant time zone, based on the examination time information in the examination information.

FIG. 8 schematically illustrates an example display screen according to the second exemplary embodiment of the present invention. Upon reception of an extraction result, the extraction result display control unit (not illustrated) of the display control unit 24 displays the imaging information input area 108 and a time-zone image capturing method list 116 (a list display method) for displaying image capturing methods extracted by the extraction unit 23 in list form, as illustrated in FIG. 8. Then, the extraction result display control unit generates the image capturing method registration buttons 114, and updates the screen display.

Although, in the second exemplary embodiment, a time zone in the morning and a time zone in the afternoon are defined, the time zone definition is not limited thereto. Further, similar processing can be performed even with the definition of the day of week, month, season, etc.

According to the second exemplary embodiment, it becomes possible to extract one or more image capturing methods frequently used in the examination time zone and display the image capturing method registration buttons 114 as described above, thus facilitating registration of image capturing methods.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-042539 filed Feb. 28, 2011, which is hereby incorporated by reference herein in its entirety.

What is claimed is:

1. A radiation imaging system for applying radiation photography to a patient based on contents of an examination request, the radiation imaging system comprising:
an image capturing method storage unit to prestore a first plurality of image capturing methods;
a patient information input unit to input patient information of the patient subjected to examination based on the examination request;
an extraction unit to extract a second plurality of image capturing methods from the first plurality of image capturing methods based on an imaging history of the patient information;
a display control unit to display a first region including a subset of the first plurality of image capturing methods in list form and a second region including at least one of the second plurality of the image capturing methods extracted by the extraction unit in list form on a screen at the same time; and
a registration unit to, by specifying the image capturing method displayed in the list of the first region and the list of the second region by the display unit, register the specified image capturing method as imaging information,
wherein each image capturing method includes an imaging portion and a type of exchangeable sensor displayed as a part of the image capturing method.

2. The radiation imaging system according to claim 1, further comprising:

an imaging information display unit to display the imaging information registered by the registration unit;
an examination generation unit to generate the examination based on the patient information and the imaging information;
an imaging control unit to control the application of radiation photography to the patient based on the examination;
an image display unit to display a radiation image acquired by the photography; and
a captured image storage unit to store a captured image related to the radiation image in association with the patient information.

3. The radiation imaging system according to claim 2, wherein the extraction unit searches, based on patient identification information accompanying the patient information, for a captured image of the relevant patient out of captured images stored in the captured image storage unit, and extracts an image capturing method of the captured image.

4. The radiation imaging system according to claim 3, wherein the imaging control unit controls the photography by using the radiation detector used to capture the captured image.

5. The radiation imaging system according to claim 3, wherein the imaging control unit controls the photography based on photographing conditions used to capture the captured image.

6. The radiation imaging system according to claim 3, wherein the imaging control unit controls display of a radiation image having undergone image processing based on image processing conditions used to capture the captured image.

7. The radiation imaging system according to claim 2, wherein information about the radiation detector used for the photography is defined for the first plurality of the image capturing methods, and
wherein the imaging control unit controls the photography by using the radiation detector.

8. The radiation imaging system according to claim 2, wherein information about photographing conditions used for the first plurality of the image capturing methods is defined for the image capturing method, and wherein the imaging control unit controls the photography based on the photographing conditions.

9. The radiation imaging system according to claim 2, wherein information about image processing conditions is defined for the first plurality of the image capturing methods, and
wherein the image display unit displays a radiation image having undergone image processing based on the image processing conditions.

10. The radiation imaging system according to claim 2, wherein the examination generation unit acquires examination information including the patient information and imaging information defining contents of photography to be applied to the patient related to the patient information, and generates the examination based on the acquired examination information; and
wherein the list display unit excludes from a target of the list display at least one of the second plurality of the image capturing methods included in the examination generated by the examination generation unit.

11. The radiation imaging system according to claim 1, wherein the extraction unit extracts, based on information about a physique of the patient accompanying the patient information, the second plurality of the image capturing methods.

12. The radiation imaging system according to claim 1, wherein the extraction unit extracts, based on examination time information accompanying the examination information, from the first plurality of the image capturing methods at least one of the second plurality of the image capturing methods used frequently in a time zone related to the examination time information.

13. The radiation imaging system according to claim 1, wherein the extraction unit extracts, based on examination date information accompanying the examination information, from the first plurality of the image capturing methods at least one of the second plurality of the image capturing methods used frequently in a date zone related to the examination date information.

14. The radiation imaging system according to claim 1, wherein the extraction unit is configured, based on requesting branch-of-medicine information accompanying the examination information, to extract from the first plurality of the image capturing methods at least one of the second plurality of the image capturing methods registered to the requesting branch-of-medicine related to the requesting branch-of-medicine information.

15. The radiation imaging system according to claim 1, wherein the list display unit excludes from a target of the list display at least one of the second plurality of the image capturing methods previously registered by the registration unit.

16. The radiation imaging system according to claim 1, wherein the extraction unit extracts from the image capturing method storage unit at least one of the second plurality of image capturing methods used frequently.

17. The radiation imaging system according to claim 1, wherein, if predetermined patient information is input by the patient information input unit, the extraction unit searches for a captured image of the predetermined patient information from a captured image storage unit, and extracts an image capturing method of the captured image.

18. The radiation imaging system of claim 1 wherein, after the specified image capturing method is registered, the display unit displays a third region containing the registered specified image capturing method on the screen.

19. The radiation imaging system of claim 1 wherein each image capturing method includes a type of sensor displayed as a part of the displayed image capturing method.

20. A method for controlling a radiation imaging system for applying radiation photography to a patient based on contents of an examination request, the method comprising:
prestoring a first plurality of image capturing methods in an image capturing method storage unit;
inputting patient information of the patient subjected to an examination based on the examination request;
extracting a second plurality of image capturing methods from the first plurality of image capturing methods based on an imaging history of the patient information;
displaying a first region including a subset of the first plurality of image capturing methods in list form and a second region including at least one of the second plurality of the extracted image capturing methods in list form in a list display unit at the same time; and
registering, by specifying the image capturing method displayed in the list of the first region and the list of the second region by the display unit, the specified image capturing method as imaging information,
wherein each image capturing method includes an imaging portion and a type of exchangeable sensor displayed as a part of the image capturing method.

21. A non-transitory computer-readable medium storing thereon a program for causing a computer to execute a method for controlling a radiation imaging system for applying radiation photography to a patient based on contents of an examination request, the method comprising:
prestoring a first plurality of image capturing methods in an image capturing method storage unit;
inputting patient information of the patient subjected to an examination based on the examination request;
extracting a second plurality of image capturing methods from the first plurality of image capturing methods based on an imaging history of the patient information;
displaying a first region including a subset of the first plurality of image capturing methods in list form and a second region including at least one of the second plurality of the extracted image capturing methods in list form in a list display unit at the same time; and
registering, by specifying an image capturing method displayed in the list of the first region and the list of the second region by the display unit, the specified image capturing method as imaging information,
wherein each image capturing method includes an imaging portion and a type of exchangeable sensor displayed as a part of the image capturing method.

22. A radiation imaging system for applying radiation photography to a patient based on contents of an examination request, the radiation imaging system comprising:
an image capturing method storage unit to store a first plurality of image capturing methods;
a patient information input unit to input patient information of the patient subjected to examination based on the examination request;
an extraction unit to extract a second plurality of image capturing methods from the first plurality of image capturing methods based on an imaging history of the patient information;
a display unit to display a first region including a subset of button related to the first image capturing methods in list form and a second region including a button related to at least one of the second plurality of the image capturing methods extracted by the extraction unit in list form on a screen at the same time; and
a registration unit to, by specifying the button displayed in the list of the first region and the list of the second region by the display unit, register the image capturing method related to the specified button as imaging information,
wherein each button includes an imaging portion and a type of exchangeable sensor displayed as a part of the button.

23. The radiation imaging system of claim 22 wherein each button, related to the first plurality of image capturing methods and at least one of the second plurality of the image capturing methods, includes a type of sensor.

24. A radiation imaging system for applying radiation photography to a patient based on contents of an examination request, the radiation imaging system comprising:
an image capturing method storage unit to prestore a first plurality of image capturing methods;
a patient information input unit to input patient information of the patient subjected to examination based on the examination request;

an extraction unit to extract a second plurality of image capturing methods from the first plurality of image capturing methods based on an imaging history of the patient information;
a display control unit to display a first region including a subset of the first plurality of image capturing methods in list form and a second region including at least one of the second plurality of the image capturing methods extracted by the extraction unit in list form on a screen; and
a registration unit to, by specifying the image capturing method displayed in the list of the first region and the list of the second region by the display unit, register the specified image capturing method as imaging information,
wherein each image capturing method includes a type of exchangeable sensor displayed as a part of the image capturing method, and
wherein the display control unit displays a third region including the specified image capturing method registered in the list of the first region and the list of the second region by the registration unit, with the first region and the second region on the screen at the same time.

* * * * *